US009784713B2

United States Patent
Shinada et al.

(10) Patent No.: US 9,784,713 B2
(45) Date of Patent: Oct. 10, 2017

(54) DISCHARGE IONIZATION CURRENT DETECTOR

(71) Applicant: SHIMADZU CORPORATION, Kyoto-shi, Kyoto (JP)

(72) Inventors: Kei Shinada, Uji (JP); Shigeyoshi Horiike, Uji (JP)

(73) Assignee: Shimadzu Corporation, Kyoto (JP)

( * ) Notice: Subject to any disclaimer, the term of this patent is extended or adjusted under 35 U.S.C. 154(b) by 741 days.

(21) Appl. No.: 13/714,070

(22) Filed: Dec. 13, 2012

(65) Prior Publication Data

US 2013/0154658 A1 Jun. 20, 2013

(30) Foreign Application Priority Data

Dec. 16, 2011 (JP) ................................. 2011-275922

(51) Int. Cl.
*G01N 27/70* (2006.01)
*G01N 27/60* (2006.01)
(Continued)

(52) U.S. Cl.
CPC .............. *G01N 27/70* (2013.01); *G01N 27/60* (2013.01); *G01N 27/66* (2013.01); *G01N 30/64* (2013.01)

(58) Field of Classification Search
CPC ........ G01N 27/62; G01N 27/66; G01N 30/64; G01N 27/70
(Continued)

(56) References Cited

U.S. PATENT DOCUMENTS 3,447,071 A * 5/1969 Beckman .................. G01K 7/40
313/146
3,526,828 A * 9/1970 Whitby .............. G01N 15/0656
324/464

(Continued)

FOREIGN PATENT DOCUMENTS

JP 2011-158357 8/2011
WO WO 2009/119050 A1 10/2009

OTHER PUBLICATIONS

Examination Report Received for Chinese Patent Application No. 201210548770.0 dated Jun. 4, 2014, 8 pages (2 pages of English Translation and 6 pages of Official Copy).

*Primary Examiner* — Jermele M Hollington
*Assistant Examiner* — Christopher McAndrew
(74) *Attorney, Agent, or Firm* — Morgan, Lewis & Bockius LLP (57) ABSTRACT

Provided is a discharge ionization current detector that is highly durable and yet can be produced at a low cost. An electrode structure 19 consisting of a dielectric-coated metal tube 16, with an insulator-coated metal wire 18 included therein, is inserted from above into a first gas passage including a dielectric tube 10. The metal tube 16 is connected to the ground on the upstream side of the first gas passage. One end of the metal wire 18 is extracted from the upstream side of the first gas passage to the outside and connected to a bias power source 33. An area which is not covered with the insulator is provided at the other end of the wire 18. This area is arranged in a second gas passage, which extends from the downstream end of the first gas passage. A metal electrode consisting of a flanged metal tube 28 is placed in the second gas passage and connected to an ion current detecting circuit 34. In the present configuration, the second gas passage, which should be heated to high temperatures, has fewer portions at which metallic parts are in (Continued)

contact with insulating members. This is advantageous for improving the durability of the device and reducing the used amount of expensive, highly heat-resistant sealing members and/or insulating members.

6 Claims, 4 Drawing Sheets

(51) Int. Cl.
*G01N 30/64* (2006.01)
*G01N 27/66* (2006.01)

(58) Field of Classification Search
USPC .......................................................... 324/464
See application file for complete search history.

(56) References Cited

U.S. PATENT DOCUMENTS

| | | | | |
|---|---|---|---|---|
| 5,394,092 | A | 2/1995 | Wentworth et al. | 324/464 |
| 5,594,346 | A * | 1/1997 | Stearns | G01N 27/70 |
| | | | | 324/455 |
| 5,892,364 | A | 4/1999 | Monagle | 324/464 |
| 6,333,632 | B1 * | 12/2001 | Yang | G01N 27/70 |
| | | | | 324/459 |
| 6,531,877 | B1 * | 3/2003 | Abdel-Rahman | G01N 27/70 |
| | | | | 324/459 |
| 6,842,008 | B2 * | 1/2005 | Stearns | G01N 27/70 |
| | | | | 324/464 |
| 7,812,614 | B2 * | 10/2010 | Kurita | G01N 27/64 |
| | | | | 324/464 |

* cited by examiner

DISCHARGE IONIZATION CURRENT DETECTOR

TECHNICAL FIELD

The present invention relates to a discharge ionization current detector primarily suitable as a detector for a gas chromatograph (GC), and more specifically to a discharge ionization current detector using a low-frequency barrier discharge.

BACKGROUND ART

As a detector for a gas chromatograph, various types of detectors have been practically applied, such as a thermal conductivity detector (TCD), electron capture detector (ECD), flame ionization detector (FID), flame photometric detector (FPD), and flame thermionic detector (FTD). Among these detectors, the FID is most widely used, particularly for the purpose of detecting organic substances. The FID is a device that ionizes sample components in a sample gas by hydrogen flame and detects the resultant ion current. It can attain a wide dynamic range of approximately six orders of magnitude. However, the FID has the following drawbacks: (1) Its ionization efficiency is low, so that its minimum detectable amount is not sufficiently low; (2) Its ionization efficiencies for alcohols, aromatic substances, and chlorine substances are low; (3) It requires hydrogen, which is a highly hazardous substance; therefore, an explosion-proof apparatus or similar kind of special equipment must be provided, which makes the entire system difficult to operate.

On the other hand, a pulsed discharge detector (PDD) has conventionally been known as a detector capable of high-sensitivity detection of various compounds from inorganic substances to low-boiling-point organic compounds, (for example, see Patent Document 1). In the PDD, the molecules of helium or another substance are excited by a high-voltage pulsed discharge. When those molecules return from their excited state to the ground state, they generate light energy. This light energy is utilized to ionize a molecule to be analyzed, and an ion current produced by the generated ions is detected to obtain a detection signal corresponding to the amount (concentration) of the molecule to be analyzed.

In most cases, the PDD can attain higher ionization efficiencies than the FID. For example, the ionization efficiency of the FID for propane is no higher than 0.0005%, whereas the PDD can achieve a high level of approximately 0.07%. However, the dynamic range of the PDD is not as wide as that of the FID; the fact is that the former is lower than the latter by one or more orders of magnitude. This is one of the reasons why the PDD is not as widely used as the FID.

The most probable constraining factors for the dynamic range of the conventional PDD are the unstableness of the plasma created for the ionization and the periodic fluctuation of the plasma state. To solve this problem, a discharge ionization current detector has been proposed (for example, refer to Patent Document 2). This detector uses a low-frequency AC-excited dielectric barrier discharge (which is hereinafter referred to as the "low-frequency barrier discharge") to create a stable and steady state of plasma. The plasma generated by the low-frequency barrier discharge is non-equilibrium atmospheric pressure plasma, which does not become hot as easily as the plasma created by the radio-frequency discharge. Furthermore, the periodic fluctuation of the plasma, which occurs due to the transition of the voltage application state if the plasma is created by the pulsed high-voltage excitation, is prevented, so that a stable and steady state of plasma can be easily obtained. Based on these findings, the present inventors have conducted various kinds of research on the discharge ionization current detector using a low-frequency barrier discharge and have made many proposals regarding this technique (for example, refer to Patent Documents 3 and 4).

Figure 5:
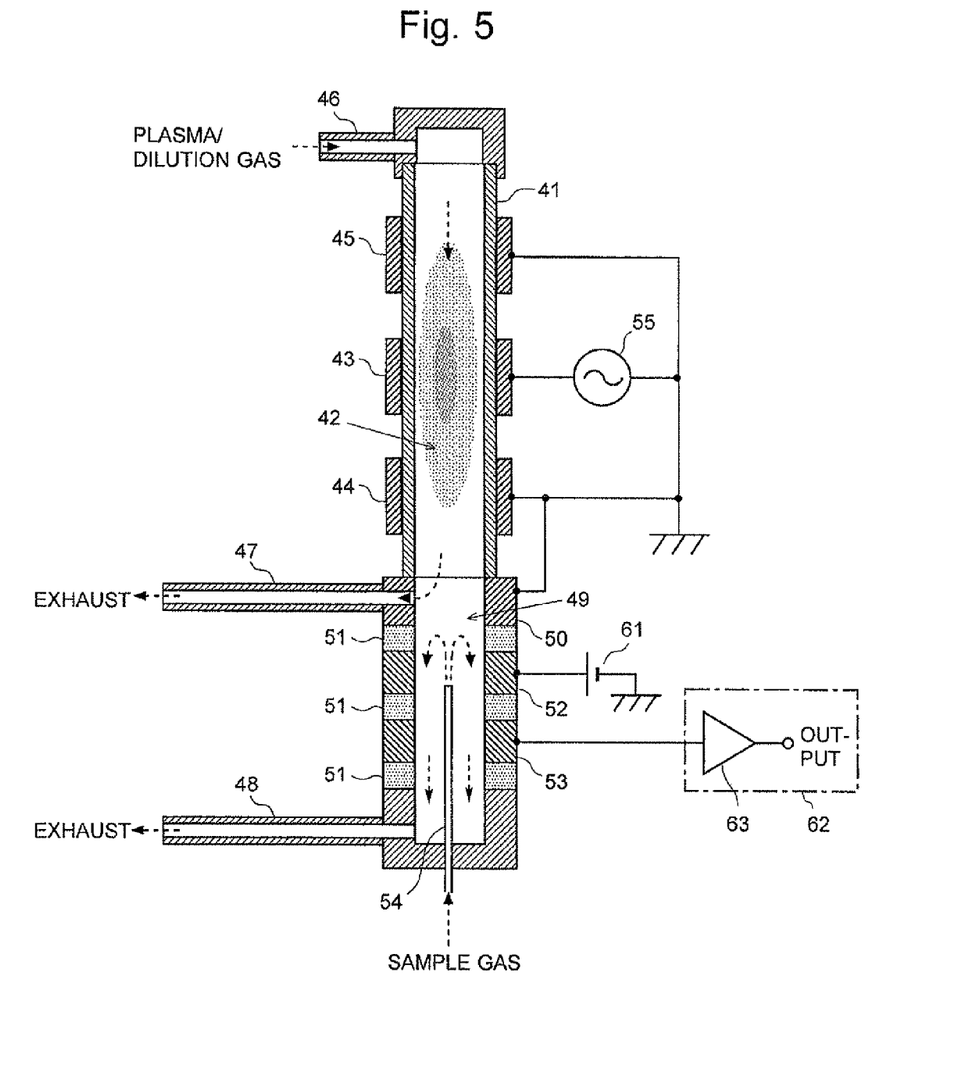
FIG. 5 is a schematic configuration diagram of a conventional discharge ionization current detector.

FIG. 5 shows one example of the conventional configuration of the discharge ionization current detector using a low-frequency barrier discharge.

This discharge ionization current detector includes a cylindrical tube 41 made of a dielectric material, such as quartz, with its inner space serving as a first gas passage 42. Ring-shaped plasma generation electrodes 43, 44 and 45 made of a metal (e.g. stainless steel or copper) are circumferentially provided at predetermined intervals on the outer wall surface of the cylindrical tube 41. According to this design, the dielectric wall of the cylindrical tube 41 between the first gas passage 42 and the plasma generation electrodes 43, 44 and 45 serves as a dielectric coating layer that covers the electrodes 43, 44 and 45, and thereby enables dielectric barrier discharge to occur.

Among the three plasma generation electrodes 43, 44 and 45, the central electrode 44 is connected to an excitation high-voltage power source 55 for generating a low-frequency high AC voltage, while the other electrodes 43 and 45 located on both sides of the central electrode 44 are connected to the ground.

In the lower portion of the cylindrical tube 41, a recoil electrode 50, a bias electrode 52 and an ion-collecting electrode 53 are arranged, with insulating members 51 provided between them. Each of these electrodes consists of a cylindrical body having the same inner diameter. These cylindrical bodies internally form a second gas passage 49 continuously extending from the first gas passage 42 in the cylindrical tube 41. Therefore, these electrodes 50, 52 and 53 are directly exposed to the gas inside the second gas passage 49. The recoil electrode 50, which is connected to the ground, prevents the charged particles in the plasma from reaching the ion-collecting electrode 53, whereby the noise is reduced and the S/N ratio is improved. The bias electrode 52 is connected to a bias DC power source 61, while the ion-collecting electrode 53 is connected to a current amplifier 63 included in an ion current detector 62. In the second gas passage 49, the space inside the bias electrode 52, the ion-collecting electrode 53 and the intervening section corresponds to the substantial current-collecting area.

A gas supply tube 46 is connected to the upper end of the cylindrical tube 41. Through this gas supply tube 46, a predetermined gas is supplied from a gas supply source (not shown) into the first gas passage 42. A first exhaust tube 47 is connected to the recoil electrode 50, which is located at the connecting portion between the first and second gas passages 42 and 49, while a second exhaust tube 48 is connected to the dead end of the second gas passage 49. A thin sample introduction tube 54 is inserted in the second gas passage 49. Through this sample introduction tube 54, a sample gas containing a sample component to be analyzed is supplied into the second gas passage 49.

A detecting operation by this discharge ionization current detector is hereinafter described. As shown by the right-pointing arrow in FIG. 5, a plasma gas, which doubles as a dilution gas, is supplied through the gas supply tube 46 into the first gas passage 42. The plasma gas doubling as the dilution gas flows downward through the first gas passage 42. At the lower end of the first gas passage 42, a portion of this gas is separated, to be eventually discharged through the first exhaust tube 47 to the outside. The remaining portion of the plasma gas serves as the dilution gas to be mixed with the sample gas and flows into the current-collecting area.

While the plasma gas is flowing through the first gas passage 42 in the previously described manner, the excitation high-voltage power source 55 is energized, whereupon the excitation high-voltage power source 55 applies a low-frequency high AC voltage between the plasma generation electrode 43 and each of the other electrodes 44 and 45. As a result, electric discharge occurs in the plasma generation area between the electrodes 44 and 45 in the first gas passage 42. This discharge is a dielectric barrier discharge since it occurs through the dielectric coating layer (i.e. the cylindrical tube 41). Due to this dielectric barrier discharge, the plasma gas flowing through the first gas passage 42 is ionized over a wide range, producing a cloud of plasma (i.e. atmospheric non-equilibrium micro-plasma).

The atmospheric non-equilibrium micro-plasma emits excitation light, which passes through the first gas passage 42 and the second gas passage 49 to the area where the sample gas exists, and ionizes the molecules (or atoms) of the sample component in the sample gas. Due to the effect of the bias DC voltage applied to the bias electrode 52, the generated sample ions give electrons to or receive electrons from the ion-collecting electrode 53. As a result, an ion current corresponding to the amount of the generated sample ions, i.e. the amount of the sample component, is sent to the current amplifier 63, which amplifies the current and outputs it as the detection signal. In this manner, the present discharge ionization current detector produces a detection signal corresponding to the amount (concentration) of the sample component contained in the introduced sample gas.

BACKGROUND ART DOCUMENT

Patent Document

Patent Document 1: US-A1 5394092
Patent Document 2: US-A1 5892364
Patent Document 3: WO 2009/119050
Patent Document 4: JP-A 2011-158357

SUMMARY OF THE INVENTION

Problem to be Solved by the Invention

When the previously described discharge ionization current detector is used as a detector in a gas chromatograph, a sample gas containing a high-boiling-point organic compound is normally introduced into the current-collecting area of the second gas passage 49. To maintain such a high-boiling-point component in a gaseous state, the second gas passage 49 is maintained at high temperatures (up to approximately 450° C.) by means of an external heater (not shown).

In the previously described discharge ionization current detector, a voltage of 100-200 V is applied to the bias electrode 52, while an extremely small amount of current at level of a few femto amperes must be detected at the ion-collecting electrode 53. Accordingly, the insulating member 51 between the bias electrode 52 and the ion-collecting electrode 53 must have a resistance of no less than a few to several tera ohms under the aforementioned high-temperature condition. For this purpose, ordinary ceramic materials are not suitable since their resistivity rapidly decreases with an increase in the temperature; and there are only limited kinds of ceramic materials that satisfy the aforementioned requirements. Therefore, it has been inevitable to use expensive materials, such as high-purity alumina or sapphire. This is one of the causes for the increase in the production cost.

It is also necessary to provide a highly airtight structure around the current-collecting area in order to prevent a penetration (leakage) of gas from the atmosphere. Therefore, at the contact surface between each of the insulating members 51 and each of the electrodes (i.e. the recoil electrode 50, the bias electrode 52 and the ion-collecting electrode 53), it is necessary to create a structure that withstands the aforementioned high temperatures while creating a sufficient air-tight condition, such as an air-tight seal using a gold-plated metal O-ring.

Another problem is the decrease in the long-term durability of the stack structure of the cylindrical insulating members 51 and the electrodes 50, 52 and 53. This problem results from various factors, such as a stress which occurs in the connection area between the insulator and the metal, the two materials having different coefficients of thermal expansion, due to the exposure of that area to the temperature cycle, or the heat effluence or wiring thermal oxidation due to the connection of electrical wiring from the hot electrodes to a circuit at room temperature.

The present invention has been developed in view of the previously described points, and its objective is to provide a discharge ionization current detector that is highly durable and yet can be produced at a low cost.

Means for Solving the Problems

A first aspect of the present invention aimed at solving the aforementioned problems is a discharge ionization current detector comprising:

a) a first gas passage through which a plasma generation gas is passed, and in which a plasma is generated from the plasma generation gas with an electric discharge;

b) a second gas passage extending from the downstream end of the first gas passage, in which a sample component in a sample gas supplied to the second gas passage is ionized by the action of the plasma;

c) a current detector for detecting an electric current due to the ionized sample component;

d) a dielectric tube forming at least a portion of the first gas passage;

e) a plasma generating excitation electrode attached to an outer circumference of the dielectric tube;

f) a metal electrode provided in the second gas passage so as to come in contact with the sample gas; and g) an electrode structure provided in the first gas passage, wherein:

the electrode structure includes a metal tube covered with a dielectric material and a metal wire covered with an insulating material and inserted in the metal tube;

the metal tube has one end electrically connected to a ground on an upstream side of the first gas passage and the other end reaching at least a point facing the plasma generating excitation electrode;

one end of the metal wire is extracted from the upstream side of the first gas passage to an outside, and the other end thereof is provided with an area that is not covered with the insulating material, the area being located within the second gas passage so as to come in contact with the sample gas; and either the aforementioned one end of the metal wire or the metal electrode is connected to a bias power source, and the remaining one is connected to an ion current detecting circuit.

The "metal tube covered with a dielectric material" may be a metal tube having a dielectric layer formed on the surface thereof, or a metal tube inserted in a tube made of a dielectric material. Similarly, the "metal wire covered with an insulating material and inserted in the metal tube" may be a metal wire having an insulating layer formed on the surface thereof, or a metal wire inserted in a tube made of an insulating material.

In the discharge ionization current detector having the previously described configuration, the area of the metal wire which is not covered with the insulating material serves as the previously described bias electrode or ion-collecting electrode. This metal wire is extracted from the upstream side of the first gas passage to the outside. This side of the first gas passage is maintained at a lower temperature than the aforementioned current-collecting area. Therefore, the discharge ionization current detector according to the first aspect of the present invention does not require such a highly heat-resistant air-tight seal or an insulating member as conventionally used at a portion through which the bias electrode or ion-collecting electrode is extracted to the outside, so that the production cost can be decreased.

The discharge ionization current detector according to the first aspect of the present invention may preferably be constructed so that:

the metal electrode has a hollow cylindrical portion with both ends open and a projecting portion extending outward in the radial direction from the outer circumference of the cylindrical portion, the cylindrical portion being arranged within the second gas passage so as to surround the area of the metal wire which is not covered with the insulating material, and the projecting portion being extracted to the outside of the second gas passage on the downstream side of the aforementioned area and connected to the bias power source or the ion current detecting circuit.

By this configuration, the ionization of a sample component in a sample gas and the detection of the thereby generated ions take place near the tip of the cylindrical portion, and the metal electrode is extracted to the outside at the projecting portion located downstream from the tip of the cylindrical portion, to be connected to an external electric wire. By this design, the portion through which the metal electrode is extracted to the outside is located downstream from the area where the ionization of the sample component and the detection of the ions take place (i.e. the current-collecting area). Therefore, even if a slight leakage of air occurs through the aforementioned portion, the air that has entered the second gas passage will be conveyed to the downstream area by the flow of gas and hence will not enter the current-collecting area. Thus, according to the present configuration, the aforementioned portion does not need to be strictly air-tight but allows the use of relatively inexpensive multi-purpose air-tight seals in place of the conventionally used gold-plated metal O-rings or other kinds of highly air-tight seals.

A second aspect of the present invention aimed at solving the aforementioned problems is a discharge ionization current detector comprising:

a) a first gas passage through which a plasma generation gas is passed, and in which a plasma is generated from the plasma generation gas with an electric discharge;

b) a second gas passage extending from the downstream end of the first gas passage, in which a sample component in a sample gas supplied to the second gas passage is ionized by the action of the plasma;

c) a current detector for detecting an electric current due to the ionized sample component;

d) a dielectric tube forming at least a portion of the first gas passage;

e) a plasma generating excitation electrode attached to an outer circumference of the dielectric tube; and f) a plurality of electrode structures inserted in the first gas passage, wherein:

each of the electrode structures includes a metal tube covered with a dielectric material and a metal wire covered with an insulating material and inserted in the metal tube;

the metal tube has one end electrically connected to a ground on an upstream side of the first gas passage and the other end reaching at least a point facing the plasma generating excitation electrode;

one end of the metal wire is extracted from the upstream side of the first gas passage to an outside, and the other end thereof is provided with an area which is not covered with the insulating material, the area being located within the second gas passage so as to come in contact with the sample gas; and one end of the metal wire included in at least one of the electrode structures is connected to a bias power source, and one end of the metal wire included in each of the other electrode structure or structures is connected to an ion current detecting circuit.

In this configuration, the portions through which the bias electrode and the ion-collecting electrode are extracted to the outside can be located on the upstream side of the first gas passage. Since none of the portions through which the aforementioned electrodes are extracted to the outside is included in the current-collecting area, which becomes hot, it is unnecessary to use a highly heat-resistant, expensive sealing member or insulating member, so that the production cost can be further reduced.

The discharge ionization current detector according to the first or second aspect of the present invention may preferably be constructed so that:

an area which is not covered with the dielectric material is provided in the other end portion of the metal tube, and this area is located downstream from the plasma generating excitation electrode and upstream from the area of the metal wire which is not covered with the insulating material.

As described previously, the one end of the metal tube is electrically connected to the ground on the upstream side of the first gas passage. The area which is not covered with the dielectric material, which is provided at the other end of the metal tube, functions as a recoil electrode for preventing the charged particles in the plasma from reaching the ion-collecting electrode. Therefore, the previously described configuration is effective for reducing the noise due to the charged particles in the plasma and thereby improving the S/N ratio.

Effect of the Invention

As described thus far, in the discharge ionization current detector according to the present invention, either the portion through which the bias electrode is extracted to the outside or the portion through which the ion-collecting electrode is extracted to the outside, or both of them, can be arranged in a relatively low-temperature area. This arrangement prevents the lowering of the durability which occurs if the contact portion between a metal electrode and an insulating member and/or the connecting portion between the electrode and an external circuit is arranged in a high-temperature area. Furthermore, the used amount of expensive sealing members and/or insulating members, such as the aforementioned gold-plated metal O-ring or high-purity alumina or sapphire, can be decreased to reduce the production cost.

BEST MODE FOR CARRYING OUT THE INVENTION

Modes for carrying out the present invention are hereinafter described by means of embodiments.

First Embodiment

Figure 1:
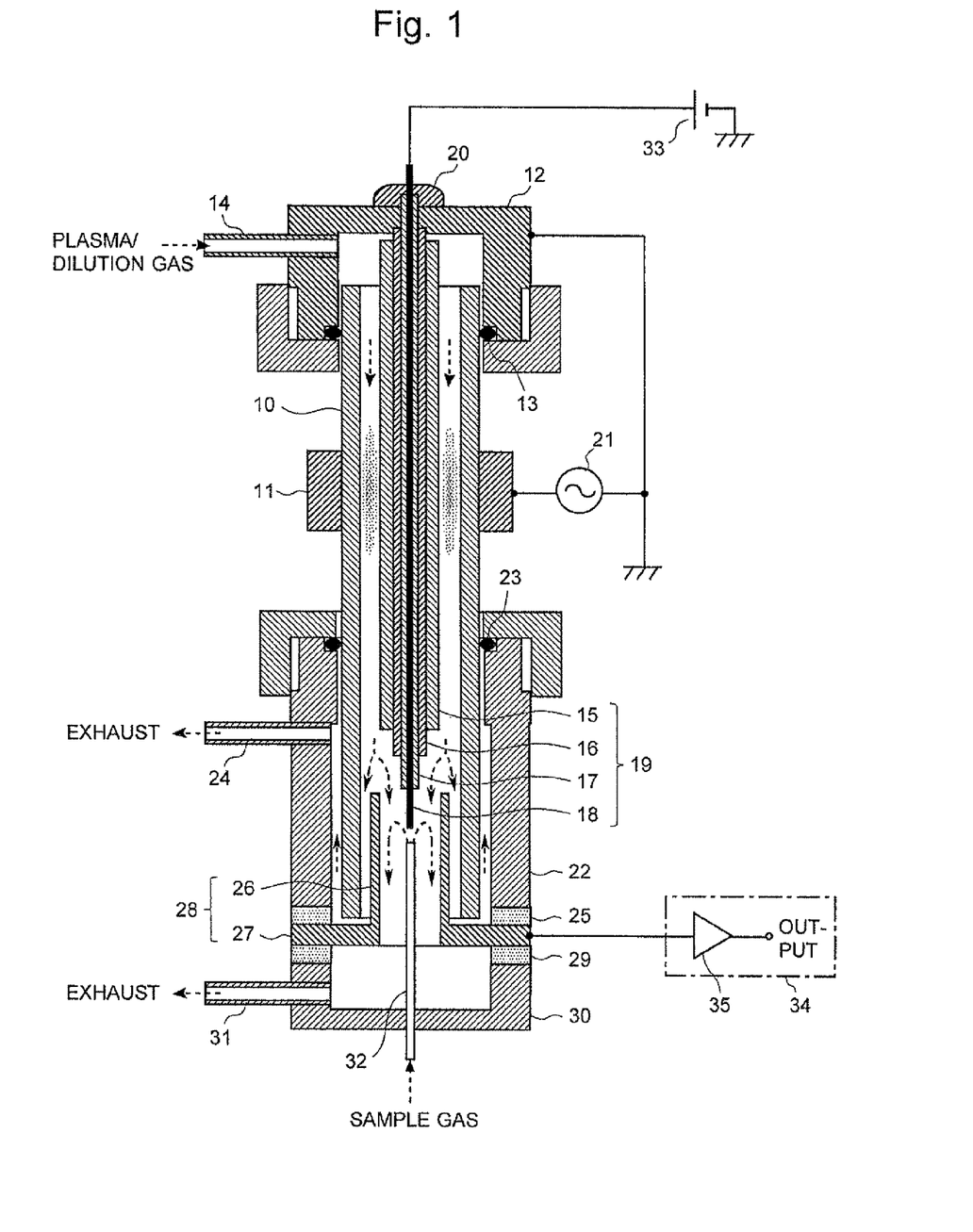
FIG. 1 is a schematic configuration diagram of a discharge ionization current detector according to the first embodiment of the present invention.

A discharge ionization current detector according to one embodiment (the first embodiment) of the present invention is hereinafter described with reference to FIG. 1. FIG. 1 is a schematic configuration diagram of a discharge ionization current detector according to the first embodiment.

The discharge ionization current detector of the present embodiment has an outer dielectric tube 10 ("dielectric tube" in the present invention) made of a dielectric material, such as quartz. For example, a quartz tube measuring 7 mm in outer diameter and 5 mm in inner diameter can be used as the outer dielectric tube 10. A ring-shaped electrode 11 ("plasma generating excitation electrode" in the present invention) made of a metal (e.g. stainless steel or copper) is circumferentially provided on the outer surface of the outer dielectric tube 10.

An upper adapter 12 in the form of a cylinder with the upper side closed and the lower side open is attached to the upper portion of the outer dielectric tube 10. The gap between the outer dielectric tube 10 and the upper adapter 12 is sealed air-tight with an O-ring 13 made of fluoro-rubber or a similar material. A gas supply tube 14 is connected to the circumferential surface of the upper adapter 12. Both the upper adapter 12 and the gas supply tube 14 are made of a metal, such as stainless steel.

Inside the outer dielectric tube 10, an inner dielectric tube 15 made of a dielectric material, such as quartz, is provided, and in which a metal tube 16 ("metal tube covered with a dielectric material" in the present invention) made of stainless steel or similar metal is inserted. Inserted in this metal tube 16 is an insulating tube 17 made of alumina or similar material, in which a metal wire 18 ("metal wire covered with an insulating material and inserted in the metal tube" in the present invention) made of a metal, such as stainless steel, is inserted. The lengths of the inner dielectric tube 15, the metal tube 16, the insulating tube 17 and the metal wire 18 are set so that the latter is longer than the former respectively in this order. More specifically, the upper and lower ends of the metal tube 16 respectively protrude from the upper and lower ends of the inner dielectric tube 15, the upper and lower ends of the insulating tube 17 respectively protrude from the upper and lower ends of the metal tube 16, and the upper and lower ends of the metal wire 18 respectively protrude from the upper and lower ends of the insulating tube 17. This structure composed of the inner dielectric tube 15, the metal tube 16, the insulating tube 17 and the metal wire 18 is hereinafter called the "electrode structure 19."

The upper adapter 12 has a through hole in its top. The upper end portion of the metal tube 16 is fixed in the through hole by welding or brazing. The insulating tube 17 and the metal wire 18 are extracted through this hole in the upper adapter 12 to the outside. The extracted portions are sealed and fixed with an air-sealing adhesive 20 on the top surface of the upper adapter 12.

The upper adapter 12 is electrically connected to the ground via an electric wire (or the gas supply tube 14). Accordingly, the metal tube 16 is also connected to the ground via the upper adapter 12. On the other hand, an excitation high-voltage power source 21 is connected to the ring-shaped electrode 11. That is to say, in the discharge ionization current detector of the present embodiment, the metal tube 16 and the ring-shaped electrode 11 function as the plasma generation electrodes. The inner circumferential surface of the ring-shaped electrode 11 and a portion of the outer circumferential surface of the metal tube 16 face each other across the walls of the outer dielectric tube 10 and the inner dielectric tube 15. This means that these walls, which are made of a dielectric material, serve as the dielectric coating layers that cover the surfaces of the plasma generating electrodes (i.e. the ring-shaped electrode 11 and the metal tube 16), thereby enabling dielectric barrier discharge to occur. The excitation high-voltage power source 21 generates a low-frequency high AC voltage, whose frequency is preferably within a range from 1 kHz to 100 kHz, and more preferably from 5 kHz to 50 kHz. The waveform of the AC voltage may be sinusoidal waves, rectangular waves, triangular waves, saw-tooth waves or any other form of waves.

The lower end of the outer dielectric tube 10 is inserted in a cylindrical intermediate adapter 22. The gap between them is sealed air-tight with an O-ring 23 made of fluoro-rubber or a similar material. A first exhaust tube 24 made of a metal, such as stainless steel, is provided in the circumferential wall of the intermediate adapter 22.

In the lower portion of the intermediate adapter 22, a cylindrical insulating member 25, a flanged metal tube 28, another cylindrical insulating member 29 and a lower adapter 30 are sequentially arranged. The flanged metal tube 28 has a cylindrical body 26 and a flange 27 extending outward in the radial direction from the lower end of the cylindrical body 26. This flanged metal tube 28 corresponds to the metal electrode in the present invention, and the cylindrical body 26 and the flange 27 respectively correspond to the cylindrical portion and the projecting portion in the present invention. The cylindrical body 26, whose outer diameter is smaller than the inner diameter of the outer dielectric tube 10, is inserted in the outer dielectric tube 10 from below. The flange 27, whose outer diameter is approximately equal to those of the intermediate adapter 22, the insulating members 25, 29 and the lower adapter 30, is held between the lower end of the intermediate adapter 22 and the upper end of the lower adapter 30 via the insulating members 25 and 29. The intermediate adapter 22, the lower adapter 30 and the flanged metal tube 28 are all made of a metal, such as stainless steel. The intermediate adapter 22, the insulating member 25, the flanged metal tube 28, the insulating member 29 and the lower adapter 30 are each adhered to the adjoining members with a ceramic type heat-resistant adhesive.

The lower adapter 30 is a cylindrical member with the top side open and the bottom side closed. A second exhaust tube 31 made of a metal, such as stainless steel, is connected to the circumferential surface of the lower adapter 30. The lower adapter 30 has a through hole in its lower side, into which a sample introduction tube 32 extending from the exit end of a gas chromatographic column is inserted. The sample introduction tube 32 is inserted into the cylindrical body 26 of the flanged metal tube 28 so that its upper end (i.e. the sample-gas exit) is located between the upper and lower ends of the cylindrical body 26.

As described previously, the metal wire 18 included in the electrode structure 19 has an exposed portion at its lower end, i.e. a portion which is not covered with the insulating tube 17. This exposed portion is inserted in the cylindrical body 26 of the flanged metal tube 28 from above and positioned near the upper end of the cylindrical tube 26. The exposed portion of the metal wire 18 is thus positioned directly above the sample-gas exit. The upper end of the metal wire 18 is extracted from the upper adapter 12 to the outside and connected to a bias DC power source 33. The flanged metal tube 28 is connected to a current amplifier 35 included in an ion current detecting unit 34 (which corresponds to the "ion current detection circuit"). That is to say, in the discharge ionization current detector of the present embodiment, the exposed portion at the lower end of the metal wire 18 serves as a bias voltage, and the cylindrical body 26 of the flanged metal electrode 28 serves as the ion-collecting electrode. This means that the space between the inner wall of the cylindrical body 26 and the exposed portion of the metal wire 18 corresponds to the substantial current-collecting area.

As described previously, the metal tube 16 included in the electrode structure 19 is connected to the ground via the upper adapter 12. The metal tube 16 has an exposed portion at its lower end, i.e. a portion which is not covered with the inner dielectric tube 15. The exposed portion, which is located directly above the flanged metal tube 28, serves as the recoil electrode for preventing the charged particles in the plasma from reaching the ion-collecting electrode (i.e. the cylindrical body 26).

In the present embodiment, the area that is inside the upper adapter 12 and the outer dielectric tube 10 as well as higher than the lower end of the inner dielectric tube 15 corresponds to the first gas passage in the present invention. The area that is inside the outer dielectric tube 10, the intermediate adapter 22 and the lower adapter 30 as well as lower than the lower end of the inner dielectric tube 15 corresponds to the second gas passage in the present invention. The second gas passage is heated up to approximately 450° C. by an external heater (not shown) to maintain the sample gas in a gaseous state.

A detecting operation by this discharge ionization current detector is hereinafter described. As shown by the right-pointing arrow in FIG. 1, a plasma gas, which doubles as a dilution gas, is supplied through the gas supply tube 14 into the upper adapter 12. The plasma gas is a gas that can be easily ionized, examples of which include helium, argon, nitrogen, neon, xenon, and any mixture of two or more of these gases.

The plasma gas doubling as the dilution gas flows downward through the space between the inner wall of the outer dielectric tube 10 and the outer wall of the inner dielectric tube 15. At the upper end of the cylindrical body 26 of the flanged metal tube 28, a portion of this gas flow is separated. The separated portion of the plasma gas flows downward through the space between the inner wall of the outer dielectric tube 10 and the outer wall of the cylindrical body 26. At the lower end of the outer dielectric tube 10, the flow direction changes outward, and then upward. Subsequently, the gas flows upward through the space between the outer wall of the outer dielectric tube 10 and the inner wall of the intermediate adapter 22, to be eventually discharged through the first exhaust tube 24 to the outside. The remaining portion of the plasma gas enters the space surrounded by the inner wall of the cylindrical body 26, where it serves as the dilution gas to be mixed with the sample gas.

While the plasma gas is flowing through the space between the inner wall of the outer dielectric tube 10 and the outer wall of the inner dielectric tube 15 in the previously described manner, the excitation high-voltage power source 21 is energized, whereupon the excitation high-voltage power source 21 applies a low-frequency high AC voltage between the ring-shaped electrode 11 and the metal tube 16, both serving as the plasma generating electrodes. As a result, electric discharge occurs in the plasma generation area between the ring-shaped electrode 11 and the metal tube 16. This discharge is a dielectric barrier discharge since it occurs through the dielectric coating layers (the outer and inner dielectric tubes 10 and 15). Due to this dielectric barrier discharge, the plasma gas flowing through the space between the inner wall of the outer dielectric tube 10 and the outer wall of the inner dielectric tube 15 (i.e. through the first gas passage) is ionized, producing a cloud of plasma (i.e. atmospheric non-equilibrium micro-plasma).

The atmospheric non-equilibrium micro-plasma emits excitation light, which passes through the space between the inner wall of the outer dielectric tube 10 and the outer wall of the inner dielectric tube 15 to the region where the sample gas exists, and ionizes the molecules (or atoms) of the sample component in the sample gas. Due to the electric field created by the bias electrode (i.e. the exposed portion of the metal wire 18) located directly above the sample-gas exit, the sample ions generated by the ionization are attracted to the ion-collecting electrode (i.e. the cylindrical body 26 of the flanged metal tube 28), to be detected as a current output. As a result, an ion current corresponding to the amount of the generated sample ions, i.e. the amount of the sample component, is sent to the current amplifier 35, which amplifies this current and outputs it as the detection signal. In this manner, the present discharge ionization current detector produces a detection signal corresponding to the amount (concentration) of a sample component contained in the introduced sample gas.

The effects achieved by the configuration of the present embodiment are as follows. In the discharge ionization current detector of the present embodiment, the metal wire 18, which serves as the bias electrode, is extracted through the top portion of the upper adapter 12 to the outside. This top portion is located on the upstream side of the flow of the plasma gas serving as the dilution gas (this flow of gas is hereinafter called the plasma-gas stream), and no sample gas passes through it. Therefore, unlike the areas on the downstream side of the plasma-gas stream i.e., the second gas passage, this area does not need to be heated to such high temperatures as to maintain the sample component in a gaseous state. Accordingly, in the present embodiment, the air-tight seal between the bias electrode and the casing of the detector (i.e. between the metal wire 18 and the upper adapter 12) does not need to be as resistant to heat as in the conventional cases; an inexpensive seal having a relatively low heat resistance, such as the aforementioned air-sealing adhesive 20, can be used as the air-tight seal for the bias electrode in place of the conventionally used gold-plated metal O-ring or similar highly heat-resistant seals. For this portion, an air-tight seal using an O-ring made of a fluorinated material or the like is also usable other than the air-sealing adhesive.

In the discharge ionization current detector of the present embodiment, the bias electrode (the meal wire 18) is inserted in the electrically grounded metal tube 16 and inserted from the upstream side of the plasma-gas stream into the first and second gas passages. Even if the resistance of the tip of the insulating tube 17 decreases due to a high temperature and allows an increase in the leakage current from the bias electrode (the metal wire 18), the entire amount of this current flows through the grounded metal tube 16 and will never flow into the ion-collecting electrode. Therefore, it is unnecessary to use a high-resistance ceramic (e.g. a high-purity alumina or sapphire) which has conventionally been necessary to insulate the ion-collecting electrode from the bias electrode. The intended role of the insulating tube 17 is thus to electrically separate the grounded metal tube 16 from the biased metal wire 18 with high resistivity. Accordingly, it is unnecessary to entirely cover the surface of the metal wire 18 with the insulating tube 17. For example, the insulating tube 17 may be constructed by arranging a plurality of short alumina sleeves inside the metal tube 16 in such a manner that the metal wire 18 does not come in contact with the metal tube 16.

The flanged metal tube 28, which serves as the ion-collecting electrode, is provided on the downstream side of the plasma-gas stream (i.e. in the second gas passage). As described previously, the second gas passage is heated to high temperatures. Accordingly, similar to the conventional case, the air-tight seal between the flange 27 of the flanged metal tube 28 and the insulating member 25 or 29 must have a relatively high heat resistance. The flanged metal tube 28, which consists of the cylindrical body 26 standing on the flange 27, is placed so that the ionization of a sample gas and the detection of the ion current take place near the upper end of the cylindrical body 26. The contact areas of the flange 27 and the insulating members 25 or 29 are located on the downstream side of the plasma-gas stream with respect to the area where the ionization of a sample gas and the detection of the ion current take place (i.e. the current-collecting area). Even if a slight leakage of air occurs through the contact area, the air that has entered the second gas passage will be conveyed into the downstream areas by the flow of gas and hence cannot reach the current-collecting area, so that no rise of the base line or no increase in the amount of noise occurs. Therefore, in the present embodiment, the connecting portion between the ion-collecting electrode and the casing of the detector (i.e. the portion at which the flange 27 of the flanged metal tube 28 adjoins to the intermediate adapter 22 or the lower adapter 30 via the insulating member 25 or 29) does not need to be as strictly air-tight as in the conventional cases. Accordingly, there is no need to use an expensive heat-resistant air-tight seal, such as the conventionally used gold-plated metal O-ring, for the connecting portion; a sufficient air-tightness can be achieved, for example, by merely joining the members with a ceramic type heat-resistant adhesive in the aforementioned manner.

In the present embodiment, it is the intermediate adapter 22 and the lower adapter 30 that are adjacent to the flange 27 of the flanged metal tube 28 via the insulating members 25 and 29. Since both of these adapters are connected to the ground, a leakage current barely flows even if the insulating material used for the insulating members 25 and 29 has a relatively low resistivity. Accordingly, it is unnecessary to use a high-resistivity ceramic or similar parts which have conventionally been used as the insulating members between the ion-collecting electrode and the casing of the detector. For example, in the discharge ionization current detector of the present embodiment, it is possible to use relatively inexpensive insulating members made of alumina or other materials.

In the above-mentioned example, the metal wire 18 is made to function as the bias voltage, and the flanged metal tube 28 as the ion-collecting electrode. These combinations can be reversed; that is to say, it is possible to connect the metal wire 18 to the current amplifier 35 and the flanged metal tube 28 to the bias DC power source 33.

In place of the flanged metal tube 28, a cylindrical metal electrode, similar to the conventional ones, may be provided as the ion-collecting electrode or bias electrode. However, in this case, the influence of the air on the current-collecting area is not negligible. Therefore, as in the conventional cases, it is necessary to adopt a highly air-tight structure in the connecting portion between the electrode and the casing of the detector.

Second Embodiment

Figure 2:
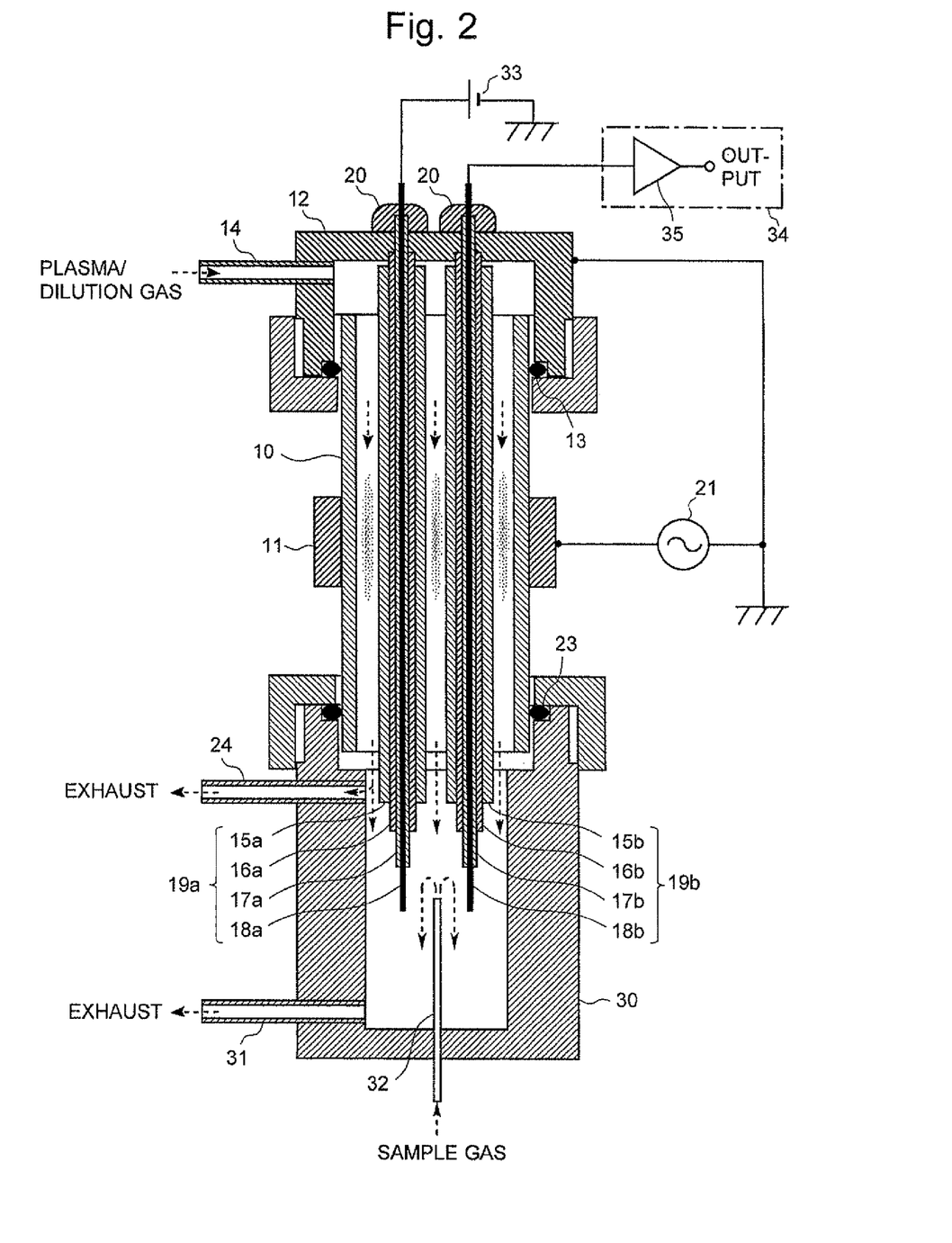
FIG. 2 is a schematic configuration diagram of a discharge ionization current detector according to the second embodiment of the present invention.

A discharge ionization current detector according to another embodiment (the second embodiment) of the present invention is hereinafter described with reference to FIG. 2. FIG. 2 is a schematic configuration diagram of the discharge ionization current detector according to the second embodiment. In this figure, the same components as used in the first embodiment are denoted by the same numerals, and the descriptions for such components will be appropriately omitted.

The discharge ionization current detector according to the present embodiment differs from the first embodiment in that the present detector has two electrode structures, that no flanged metal tube is used, and that the intermediate and lower adapters are replaced by one integral component (which is hereinafter called the "lower adapter 30").

Each of the two electrode structures in the present embodiment (which will be hereinafter called the "first electrode structure 19a" and the "second electrode structure 19b") has the same configuration as the electrode structure 19 of the first embodiment. That is to say, the electrode structure 19a or 19b has a metal tube 16a or 16b inserted in an inner dielectric tube 15a or 15b, an insulating tube 17a or 17b inserted in the metal tube 16a or 16b, and a metal wire 18a or 18b inserted in the insulating tube 17a or 17b. The upper and lower ends of the metal tube 16a or 16b respectively protrude from the upper and lower ends of the inner dielectric tube 15a or 15b. Similarly, the upper and lower ends of the insulating tube 17a or 17b respectively protrude from the upper and lower ends of the metal tube 16a or 16b, and the upper and lower ends of the metal wire 18a or 18b respectively protrude from the upper and lower ends of the insulating tube 17a or 17b.

The upper adapter 12 has two through holes in its top. The upper end portions of the metal tubes 16a and 16b are fixed in these through holes by welding or brazing to hold the first and second electrode structures 19a and 19b inside the outer dielectric tube 10. The insulating tubes 17a and 17b as well as the metal wires 18a and 18b are extracted through the two holes to the outside. The extracted portions are individually sealed and fixed with an air-sealing adhesive 20 on the top surface of the upper adapter 12.

As described previously, each of the metal wires 18a and 18b included in the electrode structures 19a and 19b has an exposed portion at its lower end, i.e. a portion which is not covered with the insulating tube 17a or 17b. This exposed portion is inserted in the lower adapter 30 from above and located at approximately the same level as the upper end of the sample introduction tube 32. The first metal wire 18a included in the first electrode structure 19a has its upper end connected to the bias DC power source 33, while the second metal wire 18b included in the second electrode structure 19b has its upper end connected to the current amplifier 35 included in the ion current detecting unit 34. That is to say, in the discharge ionization current detector of the present embodiment, the exposed portion at the lower end of the first metal wire 18a serves as the bias electrode, while the exposed portion at the lower end of the second metal wire 18b serves as the ion-collecting electrode. Accordingly, the space around the lower ends of the two metal wires 18a and 18b corresponds to the substantial current-collecting area.

The metal tubes 16a and 16b included in the electrode structures 19a and 19b are electrically connected to the ground via the upper adapter 12. Each of the metal tubes 16a and 16b has an exposed portion at its lower end, i.e. a portion which is not covered with the inner dielectric tube 15a or 15b. These exposed portions, which are located directly above the current-collecting area, serve as the recoil electrodes for preventing the charged particles in the plasma from reaching the ion-collecting electrode. Similar to the previous embodiment, the area that is inside the upper adapter 12 and the outer dielectric tube 10 as well as higher than the lower ends of the inner dielectric tubes 15a and 15b corresponds to the first gas passage in the present invention, while the area that is inside the outer dielectric tube 10 and the lower adapter 30 as well as lower than the lower ends of the inner dielectric tubes 15a and 15b corresponds to the second gas passage in the present invention. The second gas passage is heated up to approximately 450° C. by an external heater (not shown) to maintain the sample gas in a gaseous state.

In the present configuration, both the contact area of the bias electrode and the casing of the detector and that of the ion-collecting electrode and the casing the detector are arranged on the upstream side of the plasma-gas stream. This arrangement eliminates the air-tight seals between insulating members and metal electrodes which have conventionally been provided in the high-temperature area (i.e. in the second gas passage). Therefore, it is unnecessary to use a highly heat-resistant air-tight seal or an insulating member capable of showing a high insulating performance under high temperatures, so that the production cost can be further reduced.

Figure 3:
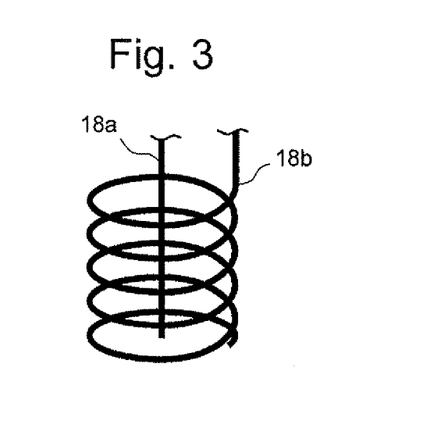
FIG. 3 is a model diagram showing one example of the shape of the electrodes in the second embodiment.
Figure 4:
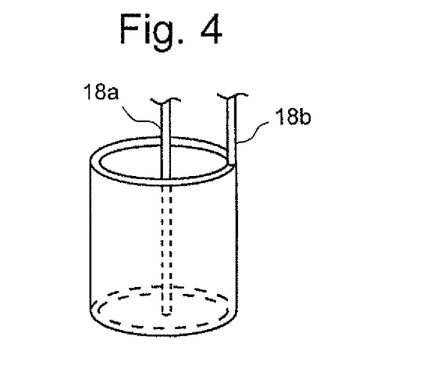
FIG. 4 is a model diagram showing another example of the shape of the electrodes in the second embodiment.

In the discharge ionization current detector of the present embodiment, the portion serving as the bias electrode or ion-collecting electrode (i.e. the lower end of the metal wire 18a or 18b) may be shaped differently from the one shown in FIG. 2. For example, as shown in FIG. 3 or 4, one of the electrodes may be shaped like a coil or cylinder to increase its surface area. More specifically, the lower end portion of the metal wire 18b serving as the ion-collecting electrode may be shaped like a cylinder or coil, with the lower end of the metal wire 18a serving as the bias electrode inside the cylinder or coil. By this configuration, the ion current will be efficiently collected.

The example shown in FIG. 2 has two electrode structures. However, it is also possible to provide the detector with three or more electrode structures. In this case, a plurality of ion-collecting electrodes can be arranged around one bias electrode so as to improve the efficiency of collecting the ion current.

Modes for carrying out the present invention have been described thus far by means of the embodiments. It should be noted that the present invention is not limited to the above-mentioned embodiments; they may be appropriately changed within the spirit and scope of the present invention. For example, in the previous embodiments, it is possible to omit the first exhaust tube 24 provided near the boundary between the first and the second gas passages, leaving only the second exhaust tube 31 provided in the downstream portion of the second gas passage. Furthermore, in the discharge ionization current detector according to any of the previous embodiments, the portion serving as the recoil electrode (i.e. the exposed portion at the lower end of the metal tube 16, 16a or 16b) may be omitted. That is to say, the metal tube may be entirely covered with the dielectric material to the lowest portion thereof.

EXPLANATION OF NUMERALS

10 . . . Outer Dielectric Tube
11 . . . Ring-Shaped Electrode
12 . . . Upper Adapter
14 . . . Gas Supply Tube
15, 15a, 15b . . . Inner Dielectric Tube
16, 16a, 16b . . . Metal Tube
17, 17a, 17b . . . Insulating Tube
18, 18a, 18b . . . Metal Wire
19 . . . Electrode Structure
19a . . . First Electrode Structure
19b . . . Second Electrode Structure
20 . . . Air-Sealing Adhesive
21 . . . Excitation High-Voltage Power Source
22 . . . Intermediate Adapter
24 . . . First Exhaust Tube
25, 29 . . . Insulating Member
26 . . . Cylindrical Body
27 . . . Flange
28 . . . Flanged Metal Tube
30 . . . Lower Adapter
31 . . . Second Exhaust Tube
32 . . . Sample Introduction Tube
33 . . . Bias DC Power Source
34 . . . Ion current Detecting Unit
35 . . . Current Amplifier

The invention claimed is:

1. A discharge ionization current detector comprising:
a first gas passage through which a plasma generation gas is passed, and in which a plasma is generated from the plasma generation gas with an electric discharge;
a second gas passage extending from the downstream end of the first gas passage, in which a sample component in a sample gas supplied to the second gas passage is ionized by the action of the plasma;
a current detector for detecting an electric current due to the ionized sample component;
a dielectric tube forming at least a portion of the first gas passage;

a plasma generating excitation electrode attached to an outer circumference of the dielectric tube;

a metal electrode provided in the second gas passage so as to come in contact with the sample gas; and an electrode structure provided in the first gas passage, wherein:

the electrode structure includes a metal tube covered with a dielectric material and a metal wire covered with an insulating material and inserted in the metal tube;

the metal tube has one end electrically connected to a ground on an upstream side of the first gas passage and another end reaching at least a point facing the plasma generating excitation electrode;

one end of the metal wire is extracted from the upstream side of the first gas passage to an outside, and another end thereof is provided with an area that is not covered with the insulating material, the area being located within the second gas passage so as to come in contact with the sample gas; and either the aforementioned one end of the metal wire or the metal electrode is connected to a bias power source, and the remaining one is connected to an ion current detecting circuit.

2. The discharge ionization current detector according to claim 1, wherein:

the metal electrode has a hollow cylindrical portion with both ends open and a projecting portion extending outward in a radial direction from an outer circumference of the cylindrical portion, the cylindrical portion being arranged within the second gas passage so as to surround the area of the metal wire which is not covered with the insulating material, and the projecting portion being extracted to an outside of the second gas passage on a downstream side of the aforementioned area and connected to the bias power source or the ion current detecting circuit.

3. The discharge ionization current detector according to claim 1, wherein:

an area which is not covered with the dielectric material is provided in said another end portion of the metal tube, and this area is located downstream from the plasma generating excitation electrode and upstream from the area of the metal wire which is not covered with the insulating material.

4. The discharge ionization current detector according to claim 2, wherein:

an area which is not covered with the dielectric material is provided in said another end portion of the metal tube, and this area is located downstream from the plasma generating excitation electrode and upstream from the area of the metal wire which is not covered with the insulating material.

5. A discharge ionization current detector comprising:

a first gas passage through which a plasma generation gas is passed, and in which a plasma is generated from the plasma generation gas with an electric discharge;

a second gas passage extending from the downstream end of the first gas passage, in which a sample component in a sample gas supplied to the second gas passage is ionized by the action of the plasma;

a current detector for detecting an electric current due to the ionized sample component;

a dielectric tube forming at least a portion of the first gas passage;

a plasma generating excitation electrode attached to an outer circumference of the dielectric tube; and a plurality of electrode structures inserted in the first gas passage, wherein:

each of the electrode structures includes a metal tube covered with a dielectric material and a metal wire covered with an insulating material and inserted in the metal tube;

the metal tube has one end electrically connected to a ground on an upstream side of the first gas passage and another end reaching at least a point facing the plasma generating excitation electrode;

one end of the metal wire is extracted from the upstream side of the first gas passage to an outside, and another end thereof is provided with an area which is not covered with the insulating material, the area being located within the second gas passage so as to come in contact with the sample gas; and one end of the metal wire included in at least one of the electrode structures is connected to a bias power source, and one end of the metal wire included in each of another electrode structure or structures is connected to an ion current detecting circuit.

6. The discharge ionization current detector according to claim 5, wherein:

an area which is not covered with the dielectric material is provided in said another end portion of the metal tube, and this area is located downstream from the plasma generating excitation electrode and upstream from the area of the metal wire which is not covered with the insulating material.

* * * * *